United States Patent [19]

Shevel

[11] Patent Number: 5,370,656
[45] Date of Patent: Dec. 6, 1994

[54] THROAT PACK

[75] Inventor: Elliot Shevel, Randburg, South Africa

[73] Assignee: Merocel Corporation, Mystic, Conn.

[21] Appl. No.: 22,920

[22] Filed: Feb. 26, 1993

[51] Int. Cl.$^5$ .............................................. A61M 31/00
[52] U.S. Cl. ..................................... 606/196; 604/54; 206/440
[58] Field of Search ............... 606/196, 194, 191, 192, 606/193, 197, 198, 199; 604/362, 369, 374, 385.1, 387, 904, 54, 178; 206/438, 440, 361

[56] References Cited

U.S. PATENT DOCUMENTS

| | | |
|---|---|---|
| 2,829,648 | 4/1958 | Knapp . |
| 2,972,350 | 2/1961 | Deker . |
| 3,046,988 | 7/1962 | Moreau et al. .................... 606/196 |
| 3,566,871 | 3/1971 | Richter et al. . |
| 3,911,922 | 10/1975 | Kliger . |
| 3,977,406 | 8/1976 | Roth .................................... 604/362 |
| 4,020,844 | 5/1977 | Vickery . |
| 4,098,728 | 7/1978 | Rosenblatt ......................... 604/369 |
| 4,844,259 | 7/1989 | Glowczewskie et al. ........... 206/440 |
| 4,883,465 | 11/1989 | Brennan ............................. 604/96 |
| 5,011,474 | 4/1991 | Brennan ............................. 604/54 |
| 5,207,651 | 5/1993 | Snyder ................................ 604/178 |

FOREIGN PATENT DOCUMENTS 1579860 11/1980 United Kingdom .

OTHER PUBLICATIONS

Mentor Advertisement, "The Merocel Ear Wick".

Primary Examiner—Tamara L. Graysay
Attorney, Agent, or Firm—Gipple & Hale

[57] ABSTRACT

A surgical sponge for use in the larynx of a throat comprising a porous cellular absorbent sponge material pre-formed in a compressed rigid member which retains its compressed small volume condition. The surgical sponge is constructed of cellular absorbent sponge material which wicks up fluid from the body to expand from compressed condition to a predetermined larger size to form an arcuate elongated body with flat end surfaces and a "C" shaped cross section defining a concave channel, at least one of the flat end surfaces being coated with a fluid impervious layer which prevents the flow of fluid therethrough. The sponge material is impregnated with a radiopaque material such as barium sulfate, and is provided with an attaching cord allowing removal of the sponge body from the patient.

20 Claims, 3 Drawing Sheets

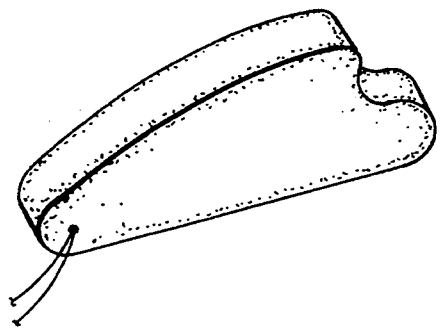
FIG. 1
(PRIOR ART)
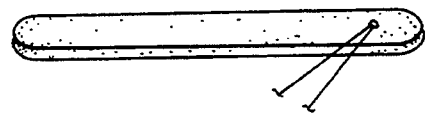
(PRIOR ART) FIG. 2
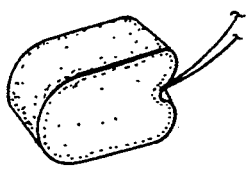
FIG. 3
(PRIOR ART)
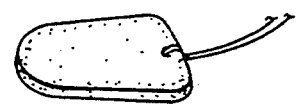
FIG. 4
PRIOR ART
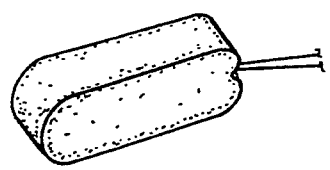
FIG. 5
(PRIOR ART)
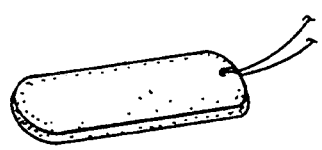
FIG. 6
(PRIOR ART)

THROAT PACK

BACKGROUND OF THE INVENTION

The present invention generally relates to surgical sponges and more directly relates to a cellular throat sponge which when placed in the larynx of the throat absorbs fluids to swell forming a specifically configured sponge. The expanded sponge is adapted to occupy a specific position at the level of the oropharynx within the larynx of the throat to surround a balloon catheter, endotracheal tube, or other medical tubing which is inserted down the throat for a surgical procedure.

The present inventive sponge also relates to a surgical throat sponge of the type used to prevent blood and other materials from passing down the throat of the patient during the oral surgery and the like.

There are currently several general types of throat packs being commonly used during oral surgery. The first being an absorptive gauze pack and the other being a tampon similar to the type used by women during their menstrual period.

Both of these throat packs and in particular the gauze pack which is the most frequently used, are known to cause damage to the throat lining during insertion and removal. Gauze pads have many disadvantages. The lint from same may pick-up bacteria from non-sterile sections of the operating room and then serve as a carrier of bacteria into the exposed body cavity of the operative patient or create undesirable foreign body reactions such as granulomata or adhesions. Since gauze pads are used to sponge organs and tissues and to pack the same during surgery, the intimate contact can cause serious trauma to the same because of their abrasiveness. As the packs absorb blood and other body fluids, they become progressively less pliable and harder, thus tending to continue their undesirable abrasive affect.

There have been many uses of sponge type devices in the medical art. U.S. Pat. No. 4,02 0,844 to Vickery discloses the use of a throat pack for use in general anaesthesia comprising a resilient molding of polymeric foam material having a triangular and semi-conical shape adapted for insertion into and occlusion of the oro-pharynx or laryngo-pharynx. The purpose of the throat pack is to resist backward displacement of the tongue. The throat pack is preferably provided with a very thin outer moisture-impermeable layer, at least on its posterior surface by applying a coating of polyurethane. An exposed region of the foamed material is used to absorb fluids and one or more safety tapes are incorporated in the throat pack so as to extend outwards through the mouth.

U.S. Pat. No. 3,911,922 to Kliger discloses a surgical sponge with a porous fabric coated on both sides with an aqueous liquid absorbing flexible foamed polymer. A X-ray detectable material is provided next to the fabric and a loop handle is stitched to one side of the sponge through the foam layers. U.S. Pat. No. 3,566,871 to Richter et al. shows a hydrophilic polyurethane sponge adapted for medical usage with the sponge pores containing a surfactant coating to accelerate absorption of body fluids into the pores, the fluids being retained therein by capillarity to affect removal of the fluids from the body. The sponge can be cut into a number of different shapes for ophthalmic, neurosurgery and other medical applications and is provided with a radiopaque tracer filament or tracer material incorporated into the foam during its formation.

U.S. Pat. No. 2,972,350 to Decker discloses a surgical sponge of a roll of absorbent material bent into the form of a "U" and having its ends secured together. The material may be synthetic cellular sponge material or cotton rolls and the sponge is constructed with a thread or strip of X-ray opaque material passed through the roll. Other suitable materials such as thermoplastic threads, strips of cellulose esters, vinyl chloride polymers, polymers of acrylic acid, polymers of acrylic acid esters and their derivatives which have dispersed through them very finely divided particles of barium sulfate can be used.

U.S. Pat. No. 2,829,648 to Knapp shows a surgical sponge of balled absorbent cotton fibers, or woven cotton gauze wrapped in a swatch of sheet material such as surgical gauze to provide a hemostatic covering for the sponge.

The Merocel Corporation has used a number of surgical sponges made of the MEROCEL sponge material and such sponges are shown as prior art and are illustrated by the drawings of FIGS. 1-6.

SUMMARY OF THE INVENTION

A surgical sponge for use in a throat cavity comprising a porous cellular absorbent sponge material prepackaged to provide a compressed rigid member which retains its compressed small volume condition for optional insertion into the body cavity. The sponge member is constructed of cellular absorbent sponge material which wicks up fluid from the body or through pre hydration to expand from the initial compressed condition to a predetermined larger size to form an arcuate elongated body with flat end surfaces having a "C" shaped cross section providing an internal arcuate channel. At least one of the flat end surfaces are coated with a fluid impervious coating or layer which prevents the flow of fluid therethrough. The sponge material is impregnated with an radiopaque material such as barium sulfate, and is provided with an attaching cord having a clamp assembly at or near one end, the other end being secured to the sponge body, the attaching cord having a length such that the end remote from the sponge can be disposed outside of the throat cavity of the patient.

One object of the invention is to provide a new throat pack configuration utilizing synthetic expandable sponge material which eliminates or decreases damage to the throat lining after insertion and removal.

Another object of the invention is to provide synthetic resilient sponge material for a throat pack for the oropharynx having a configuration which is convex to conform to the anterior of the oropharynx and concave toward the posterior of the oropharynx with a cross sectional configuration being "C" shaped. The dimensions of the cross sectional configuration are larger than the corresponding dimensions of the throat in which the pack is intended for use and include a channel for accommodating an endotracheal tube along the length of the surgical sponge so that the sponge and endotracheal tube in the sponge channel form a substantially linear line.

Another object of the invention is to include an impervious layer at one end of the throat pack which prevents fluid from passing down to the stomach. Yet another object of the invention is to provide a disposable sponge which will rapidly absorb up to about 25 times its dry weight of fluids.

In the accompanying drawings, there is shown an illustrative embodiment of the invention from which these and other of objectives, novel features and advantages will be readily apparent.

BRIEF DESCRIPTION OF THE DRAWINGS

FIG. 1 is an expanded prior art nasal pack device;

FIG. 2 is the compressed form of the device of FIG. 1.

FIG. 3 is an expanded prior art sinus-pak device;

FIG. 4 is the compressed form of the device of FIG. 3.

FIG. 5 is a prior art expanded nasal pack device;

FIG. 6 is the compressed form of the device of FIG. 5.

DETAILED DESCRIPTION OF THE EMBODIMENT

Figure 7:
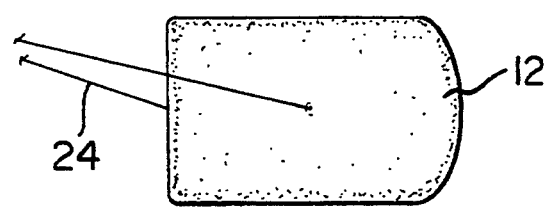
FIG. 7 is a perspective view of the invention in its normal compressed packaged state.
Figure 8:
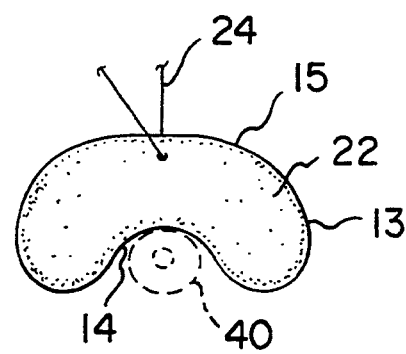
FIG. 8 is a top plan view of the expanded inventive sponge shown in FIG. 7.
Figure 9:
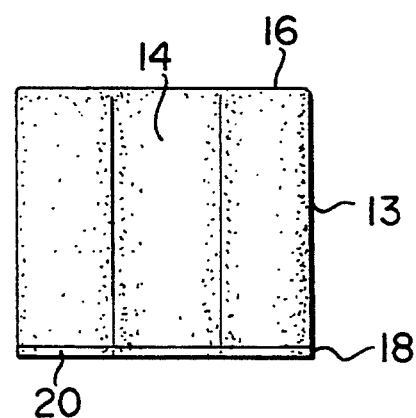
FIG. 9 is a front elevational view of the sponge positioned in plan view in FIG. 8.
Figure 10:
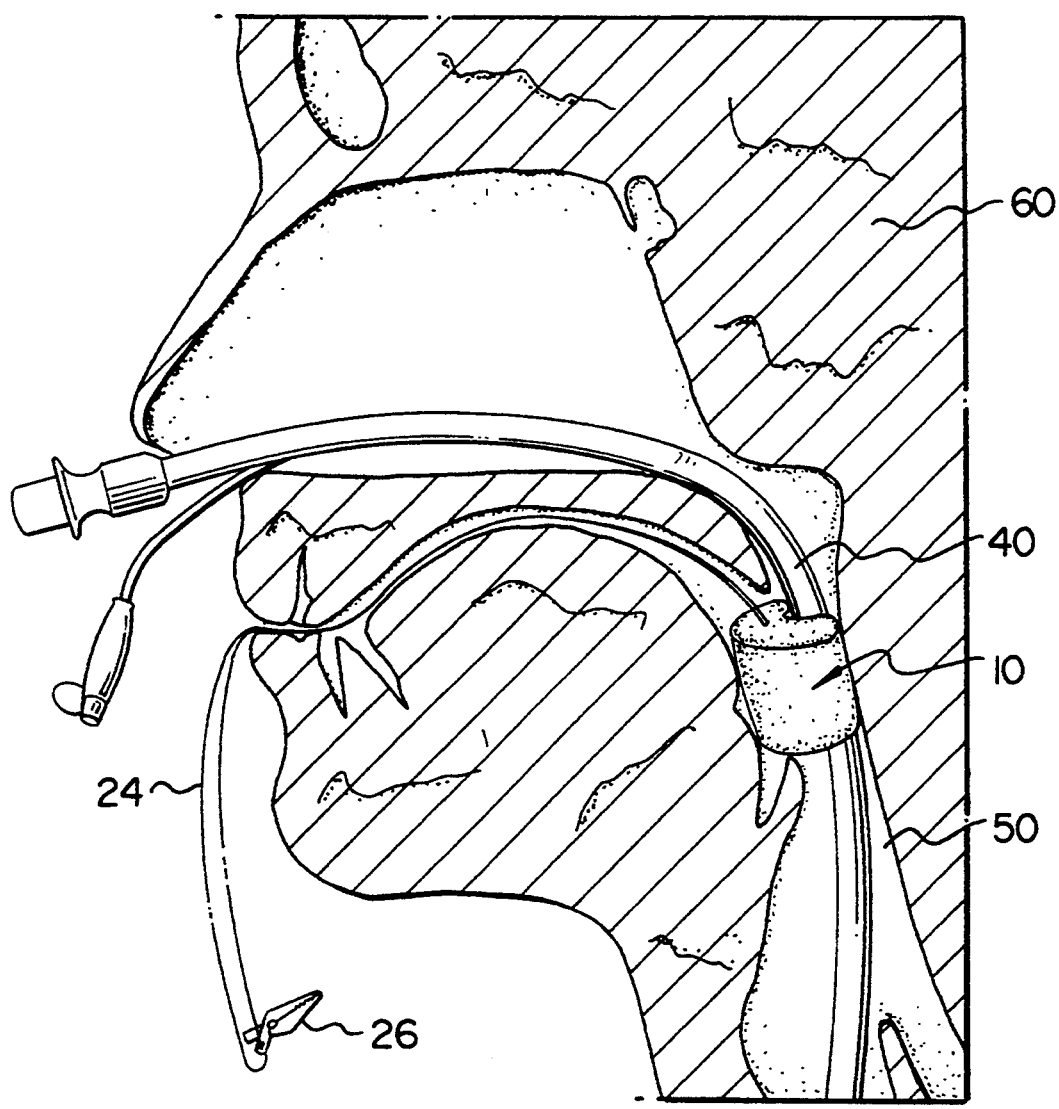
FIG. 10 is a schematic view of the inventive sponge device shown placed in the oropharynx of the larynx of a patient.

The preferred embodiment and best mode of the invention is shown in FIGS. 7 through 10. In the invention, a throat pack 10 is provided for use in closing the throat 50 of a patient 60 undergoing oral surgery or the like. The throat sponge member 10 is constructed of compressed hydroxylated polyvinyl acetal (PVA) material having a controlled pore size uniformly distributed throughout its volume which is fast wicking and has a high liquid holding capacity. The sponge material has an instantaneous absorbency time and expands uniformly to absorb water or other fluids in a range 23 to 27 times the sponge weight. The material is marketed under the trademark MEROCEL by the Merocel Corporation and the material is specifically described by U.S. Pat. No. 4,098,728 issued Jul. 4, 1978 entitled Medical Surgical Sponge and Method of Making Same which has been assigned to the Merocel Corporation and is incorporated by reference into this application.

The throat sponge member 10 has an elongated flat relatively rigid body 12 when compressed for packaging as shown in FIG. 7. The throat sponge member can be inserted by the physician or surgeon down into the oropharynx of the larynx of the throat 50 of the patient 60. If desired the throat sponge member can be hydrated for pre insertion. The throat sponge member 10 in packaged form has a compressed flat linear body 12 with slightly curved outer edges ranging from 20–26 mm. in width and 4 mm. to 6 mm. in thickness with an average width of 23 mm. and average thickness of 4 mm. As previously noted the sponge material swells upon fluid contact so that rigid body 12 becomes flexible and pliable swelling to approximately 50 mm. in length, 50–55 mm. at its greatest width, and an average thickness of 25–27 mm. The highly flexible and soft sponge body 13 intergages with the inner walls of the larynx, aided by the natural moistness of such walls and clings thereto in a substantially fixed position closing the cavity but remaining in position without injury or discomfort to the patient while allowing easy removal by the surgeon.

The surgical sponge is radiopaque due to the inclusion of barium sulfate, bismuth suboxide or other suitable radiopaque material locked within the sponge structure or if desired the adhesive holding the fluid impermeable layer 20 onto the cellular wall structure of the sponge. If desired, a radiopaque marker band can be formed on or within the sponge. The surgical sponge 10 absorbs fluid from the throat or by pre-hydration and expands retaining flexibility until it generally corresponds to the "C" shaped cross section shown by the plan view shown in FIG. 8. The arcuate convex "C" portion of the sponge 15 generally corresponds to a "D" shaped cross section of the oropharynx through a patient's larynx as defined by cricoid cartilage. The concave portion of the "C" forms an elongated arcuate channel 14 approximately 22 mm. deep and 15 to 20 mm. in width at its lowest point and 25 to 30 mm. in width at it s upper portion running along the length of the body 13. This channel 14 is intended to accommodate an endotracheal tube or catheter 40 entering a patient's throat via the nasal orifice lying on the posterior of the larynx.

The top end 16 and bottom end 18 of the swelled or expanded surgical sponge may be selectively suitably sealed with a liquid impermeable layer 20 such as silicone rubber which is adhesively secured to the cellular structure of the surgical sponge. This liquid impervious layer 20 serves to prevent the passage of blood or other liquids into the patients throat. Adhesive or other means of affixing the layer 20 is necessary if the layer 20 comprises a composite or homogeneous body of self-sustaining independent nature. If the material to provide the liquid impervious layer is in the form of a coating which is applied by spraying, brushing or other application to the body such as by dipping the body into a solution having the necessary properties of a coating, then the adhesive may be eliminated. In addition to the silicone layer, suitable flexible liquid-impermeable materials can be used including polyolefins such as polyethylene and polypropylene, saran and the like. The remainder of the sponge material is fully exposed to allow the absorption of liquids.

At its upper flat end 22, the surgical sponge may include a short standard or radiopaque filament or cord loop 24 fixed onto the sponge body. It will be appreciated that this cord may be used for withdrawal of the surgical sponge after use. The distal end of the cord loop is fastened to an alligator clip 26 to allow for easy removal of the device and for use in securing the sponge to a procedure drape to prevent swallowing of the sponge. The surgical sponge can, of course, be available in several sizes to accommodate various size throats which one would find with people of differing ages.

In an operation, the surgical sponge is simply inserted into the patient's throat over an endotracheal tube 40 with the tube being accommodated in the channel 14 of the surgical sponge and the cord 24 extending outside the mouth of the patient. Because of the soft, flexible condition of the throat pack, it can be easily be inserted into position and will expand to essentially occlude the throat passage providing gentle equal support for catheter endotracheal tube 40. Furthermore, the low pressure provided by the sponge does not cause tissue necrosis and does not restrict gas or fluid delivery through the catheter or endo-tracheal tube. Alternately, it can be prehydrated and inserted in the throat passage. Regardless of the method of insertion, compressed or prehydrated the sponge will properly seal around any tube in the larynx. Removal of the throat pack 10 is easily accomplished using the cord 24 by grabbing the alligator clip 26 and thread or cord loop 24 and pulling the sponge body out of the larynx through the mouth of the patient.

The medical value of the present invention was shown by testing set forth in the following example:

EXAMPLE 1

A group of patients consisting of 47 patients was observed in whom a damp gauze throat pack was used. Seventeen patients had no post operative sore throat, 18 patients registered pain scores of less than 10 on the visual analog scale and 12 patients or approximately 25.5% registered scores on the visual analog scale above 10.

In the second group of 53 patients, the inventive throat packs were used. These packs were designed to fit snugly around the nasal-tracheal tube as previously mentioned to facilitate insertion and minimize trauma. Of the 53 patients in the group, 27 of these patients had no pain at all, 22 had pain scores of less than 10 on the visual analog scale and only 4 patients or approximately 7.5% had pain scores of above 10 on the visual analog scale.

Of this data, it was shown to be highly significant using the Chi-square test (p less than 0.005) (Allen 1982). Chi-square=18.3; d.f.=2.

|  | NO PAIN | PAIN SCORE LESS THAN 10 | PAIN SCORE MORE THAN 10 |
| --- | --- | --- | --- |
| GAUZE | 17 | 18 | 12 |
| THROAT PACK | 27 | 22 | 4 |
| Chi-square = 18.3; d, f, = 2. | | | |

This data, was shown to be highly significant using the Chi-squared test (p less than 0,005) (Allen 1982).

Conclusions of the study show that both the incidence and severity of post operative sore throat can be significantly reduced by using a throat pack of the present inventive nature.

In the foregoing description, the invention has been described with reference to a particular preferred embodiment, although it is to be understood that specific details shown are merely illustrative, and the invention may be carried out in other ways without departing from the true spirit and scope of the following claims:

What I claim is:

1. A uniformly swellable hydrophilic surgical throat sponge having a uniform pore geometry and pore distribution throughout its volume constructed in an initial rigid linear form, said sponge being preformed in compression so that when expanded by absorption of fluids it swells to form a flexible "C" shaped cross sectional configuration having a convex surface which is adapted to sit against the anterior surface of the larynx and a concave surface which is adapted to sit over tubing which may be positioned down the throat of a patient, thread retaining means mounted to said sponge, said thread retaining means comprising a filament with clip means mounted thereon, said clip means being adapted to be mounted to a surgical drape to prevent said surgical throat sponge from being swallowed.

2. A surgical throat sponge as claimed in claim 1 wherein said sponge is an open-celled PVA material.

3. A surgical throat sponge as claimed in claim 1 wherein said sponge material is impregnated with a radiopaque material.

4. A surgical throat sponge as claimed in claim 3 wherein said radio-opaque material is barium sulfate.

5. A surgical throat sponge as claimed in claim 1 wherein said "C" shaped sponge member has flat end surfaces.

6. A surgical throat sponge as claimed in claim 5 wherein one of said flat end surfaces is covered with a fluid impervious layer which prevents the flow of fluid therethrough.

7. A uniformly swellable hydrophilic surgical throat sponge for insertion into the larynx having a uniform pore distribution throughout its volume, said sponge being preformed in compression into a flattened form so that when it is expanded by absorbing fluids inside the throat it forms a "C" shaped cross sectional configuration with flat end sections, at least one of said end sections being provided with a fluid impervious layer to prevent fluid flow, and loop handle means secured to said sponge body, the sponge body when expanded in the larynx of the throat seating itself for sole support with the sponge body being in an intersecting covering relationship with the orifice of the larynx, said loop handle means secured to said sponge body and extending outside the patients body when the throat sponge is expanded in the larynx of the throat, and means mounted to said loop handle to prevent dislodgment and swallowing of said sponge member.

8. A surgical sponge for use in a throat cavity comprising a porous cellular absorbent sponge material pre-formed to provide a compressed rigid member which retains its compressed small volume condition for optional insertion into the body cavity, said member being constructed of cellular absorbent sponge material which wicks up fluid from the body to expand from compressed condition to a predetermined larger size to form an arcuate elongated body with flat end surfaces and a "C" shaped cross section defining an internal arcuate concave channel, at least one of said flat end surfaces being provided with a fluid impervious layer which prevents the flow of fluid therethrough, said sponge material being impregnated with a radiopaque material, and cord means for retaining the sponge body comprising an attaching cord having a stop member at one end, the other end being secured to the sponge body, said cord having a length such that the end remote from the sponge can be disposed outside of the throat orifice.

9. A surgical sponge as claimed in claim 8 wherein said at least one end provided with a fluid impervious layer is a silicon layer.

10. A surgical sponge as claimed in claim 9 wherein said impervious layer is secured to said sponge by adhesive.

11. A surgical sponge as claimed in claim 10 wherein said adhesive contains a radiopaque material.

12. A surgical sponge as claimed in claim 8 wherein said expanded sponge body has a width ranging from 50 to 55 mm and a thickness ranging from 25 to 27 mm.

13. A surgical sponge as claimed in claim 8 wherein said at least one end provided with a fluid impervious layer is a thin flexible coating.

14. A surgical sponge package comprising a compressed surgical sponge throat sponge sealed in a watertight package, a second package holding said watertight package, said surgical throat sponge having a uniform pore geometry and pore distribution throughout its volume constructed in an initial rigid linear form, said sponge being preformed in compression so that when in contact with liquid, it swells to form a flexible "C" shaped cross sectional configuration having a convex surface which is adapted to sit against the anterior surface of the larynx and a concave surface which is adapted to sit over tubing positioned down the throat of a patient.

15. A uniformly swellable hydrophilic throat sponge having a uniform pore distribution throughout its volume, said sponge being constructed in an initial rigid linear form with at least one end of said throat sponge being provided with a flexible liquid impermeable layer, said sponge being preformed in compression in said linear form allowing it to be placed inside the larynx of a patient so that when placed in the larynx it is expanded by absorption of fluids to form a flexible "C" shaped cross sectional configuration having a convex surface which is adapted to sit against the anterior surface of the larynx and a concave surface which is adapted to sit over tubing positioned in the throat of a patient to prevent fluids from freely flowing down to the stomach of said patient, and a withdrawal string mounted to said sponge allowing said sponge to be withdrawn from the larynx of the patient.

16. A uniformly swellable hydrophilic throat sponge as claimed in claim 15 wherein said concave surface of said sponge forms an elongated arcuate channel about 22 mm deep and ranging from 15 to 30 mm in width.

17. A uniformly swellable hydrophilic throat sponge as claimed in claim 15 wherein said impermeable layer is silicone rubber.

18. A uniformly swellable hydrophilic throat sponge as claimed in claim 15 wherein said impermeable layer is polyethylene.

19. A uniformly swellable hydrophilic throat sponge as claimed in claim 15 wherein said impermeable layer is polypropylene.

20. A uniformly swellable hydrophilic throat sponge as claimed in claim 15 wherein the top and bottom ends of said throat sponge are provided with a flexible liquid impermeable layer.

* * * * *